United States Patent
Hawes

(10) Patent No.: US 9,829,443 B2
(45) Date of Patent: Nov. 28, 2017

(54) CRYOSTAT INSPECTION CAMERA ARRANGEMENT AND METHOD

(71) Applicant: SIEMENS PLC, Camberley (GB)

(72) Inventor: Christopher Michael Hawes, Bicester (GB)

(73) Assignee: Siemens Healthcare Limited, Camberley (GB)

( * ) Notice: Subject to any disclaimer, the term of this patent is extended or adjusted under 35 U.S.C. 154(b) by 246 days.

(21) Appl. No.: 14/778,713

(22) PCT Filed: Feb. 14, 2014

(86) PCT No.: PCT/EP2014/052974
§ 371 (c)(1),
(2) Date: Sep. 21, 2015

(87) PCT Pub. No.: WO2014/146837
PCT Pub. Date: Sep. 25, 2014

(65) Prior Publication Data
US 2016/0054236 A1 Feb. 25, 2016

(30) Foreign Application Priority Data
Mar. 21, 2013 (GB) .................. 1305204.8

(51) Int. Cl.
| | |
|---|---|
| G01N 21/954 | (2006.01) |
| H01F 6/04 | (2006.01) |
| H04N 5/232 | (2006.01) |
| F17C 3/08 | (2006.01) |
| H04N 5/372 | (2011.01) |
| G02B 23/24 | (2006.01) |
| G01N 21/94 | (2006.01) |
| G06T 7/00 | (2017.01) |

(52) U.S. Cl.
CPC .......... *G01N 21/954* (2013.01); *F17C 3/085* (2013.01); *G01N 21/94* (2013.01); *G02B 23/2484* (2013.01); *G02B 23/2492* (2013.01); *G06T 7/001* (2013.01); *G06T 7/0008* (2013.01); *H01F 6/04* (2013.01); *H04N 5/23241* (2013.01); *H04N 5/372* (2013.01); *G01N 2201/062* (2013.01); *G06T 2207/30164* (2013.01)

(58) Field of Classification Search
CPC ..... F17C 3/085; G01N 21/94; G02B 23/2484; G02B 23/2492; G06T 7/0008; G06T 7/001; H01F 6/04; H04N 5/23241; H04N 5/372
See application file for complete search history.

(56) References Cited

U.S. PATENT DOCUMENTS

| | | | |
|---|---|---|---|
| 3,358,472 A | 12/1967 | Klipping | |
| 4,965,601 A | 10/1990 | Canty | |
| 6,196,005 B1 | 3/2001 | Stautner | |
| 6,339,026 B1 | 6/2002 | Karral | |
| 2009/0273776 A1 | 11/2009 | Bittner | |

FOREIGN PATENT DOCUMENTS

| | | | | |
|---|---|---|---|---|
| EM | EP000442285 | * | 8/1991 | ............... B67C 3/30 |
| JP | 005919842 | * | 1/2012 | ............. G01N 21/90 |

* cited by examiner

*Primary Examiner* — David F Dunphy
(74) *Attorney, Agent, or Firm* — Schiff Hardin LLP

(57) ABSTRACT

A bung assembly for closing an opening in a turret of a cryostat has a camera housing and bung body that is mechanically dimensioned to fit the opening, and is provided with a sealing arrangement for forming a gas-tight seal between the bung body and the turret.

8 Claims, 10 Drawing Sheets

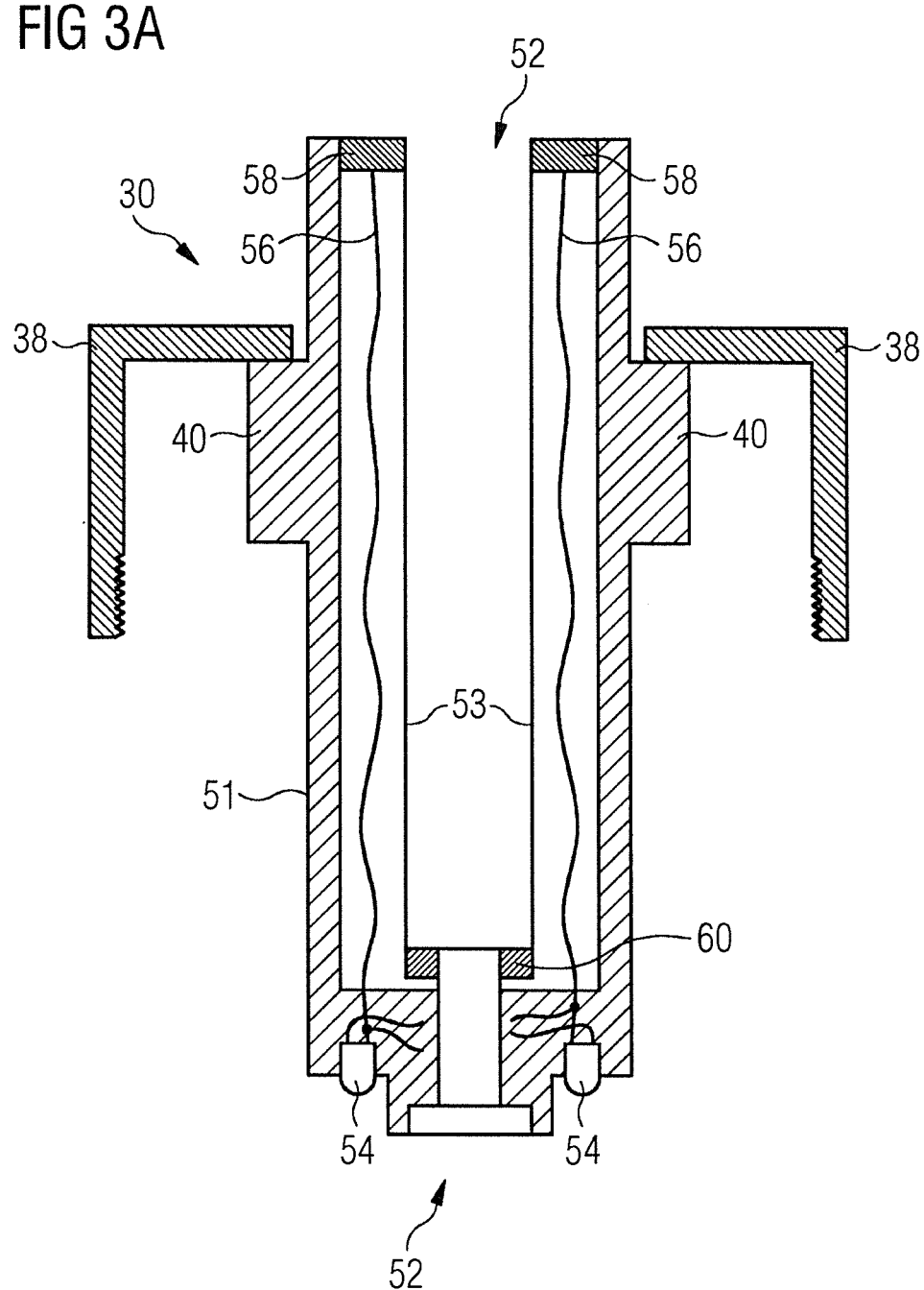

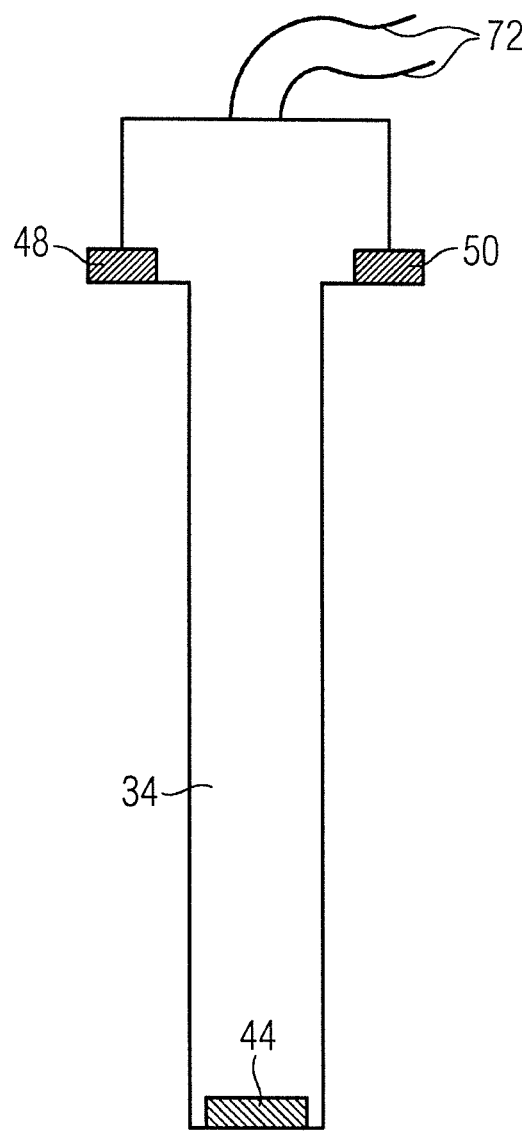

CRYOSTAT INSPECTION CAMERA ARRANGEMENT AND METHOD

BACKGROUND OF THE INVENTION

Field of the Invention

The present invention relates to arrangements for performing inspections of internal parts of a cryostat, to observe ice build-up within sensitive parts of the cryostat and to prompt preventative maintenance procedures in response to detection of ice.

Description of the Prior Art

FIG. 1 shows a conventional arrangement of a cryostat including a cryogen vessel 12. A cooled superconducting magnet 10 is provided within cryogen vessel 12, itself retained within an outer vacuum chamber (OVC) 14. One or more thermal radiation shields 16 are provided in the vacuum space between the cryogen vessel 12 and the outer vacuum chamber 14. In some known arrangements, a refrigerator 17 is mounted in a refrigerator sock 15 located in a turret 18 provided for the purpose, towards the side of the cryostat. Alternatively, a refrigerator 17 may be located within access turret 19, which retains access neck (vent tube) 20 mounted at the top of the cryostat. The refrigerator 17 provides active refrigeration to cool cryogen gas within the cryogen vessel 12, in some arrangements by recondensing it into a liquid. The refrigerator 17 may also serve to cool the radiation shield 16. As illustrated in FIG. 1, the refrigerator 17 may be a two-stage refrigerator. A first cooling stage is thermally linked to the radiation shield 16, and provides cooling to a first temperature, typically in the region of 80-100K. A second cooling stage provides cooling of the cryogen gas to a much lower temperature, typically in the region of 4-10K.

A negative electrical connection 21a is usually provided to the magnet 10 through the body of the cryostat. A positive electrical connection 21 is usually provided by a conductor passing through the vent tube 20.

For fixed current lead (FCL) designs, a separate vent path (auxiliary vent) (not shown in FIG. 1) is provided as a fail-safe vent in case of blockage of the vent tube 20.

MRI magnets in the field must be checked for any air ingress which results in ice building up inside the cryostat. The ice can build-up over a period of time. There are no set times for ice build-up to occur, and any given cryostat may not ice at all. Any ice in the cryostat is a problem and can cause problems with helium re-condensing, helium filling, venting, and quenching.

Existing equipment and methods for detecting and removing ice build-up are complex and difficult. Such checks are accordingly carried out only rarely. Icing inside the cryostat is usually found only when a magnet is serviced or has a problem for any reason, typically after a significant build-up of ice has taken place. Removal of such a large ice build-up requires significant down time and expense to correct. The necessary equipment used by an engineer is bulky and parts of the equipment are damaged easily by the cryogenic temperatures. The equipment requires the magnet to be ramped down to zero field so it can be used safely, this requires a power supply to be despatched to the site.

Known disadvantages of the conventional arrangements for checking for ice build-up include the following:

Detection only occurs once the ice has built up to such a level that it has become a problem.

If ice build-up is suspected, special bore scope equipment and power supplies must be shipped to the magnet, wherever it may be in the world, which is time consuming, complex and costly. The equipment itself is bulky and costly and so is not provided to local service technicians as part of a routine servicing kit. A specially trained service technician is required to undertake the check, which may involve significant travel and expense.

The bore scope equipment has a short life when used at cryogenic temperatures, and must be replaced frequently, although it is expensive.

Conventional methods for checking for ice build-up require that the magnet is at zero field. The equipment required for ramping a magnet down to zero field, then back up to full field after checking is costly and bulky. Such ramping down and ramping up also consumes significant amounts of cryogen.

SUMMARY OF THE INVENTION

A bung assembly for closing an opening in a turret of a cryostat has a camera housing and bung body that is mechanically dimensioned to fit the opening, and is provided with a sealing arrangement for forming a gas-tight seal between the bung body and the turret.

BRIEF DESCRIPTION OF THE DRAWINGS

FIGS. 3A and 3B illustrate the arrangement of FIG. 2 separated into two component parts.

DESCRIPTION OF THE PREFERRED EMBODIMENTS

Figure 1:
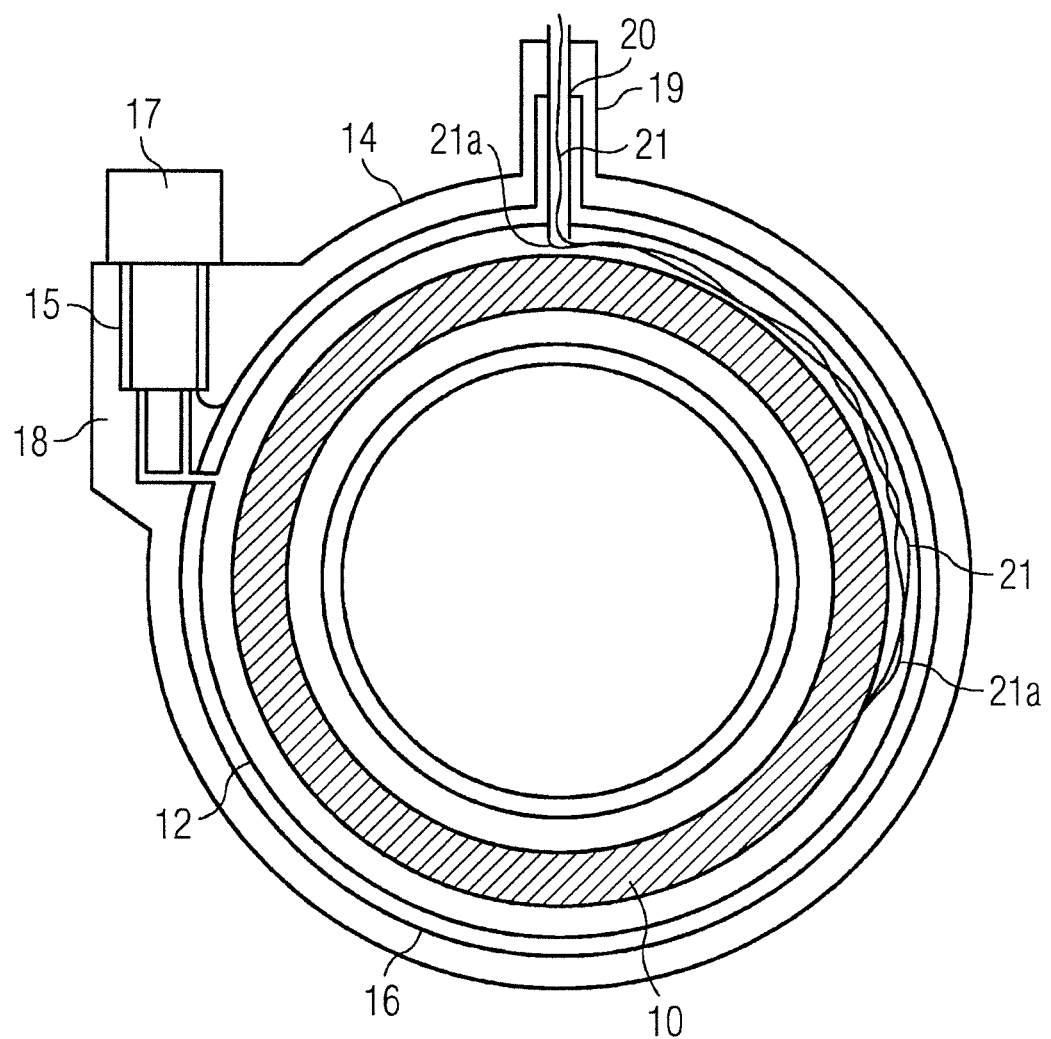
FIG. 1 schematically illustrates a known arrangement of superconducting magnet in a cryostat, as used in MRI systems.
Figure 5:
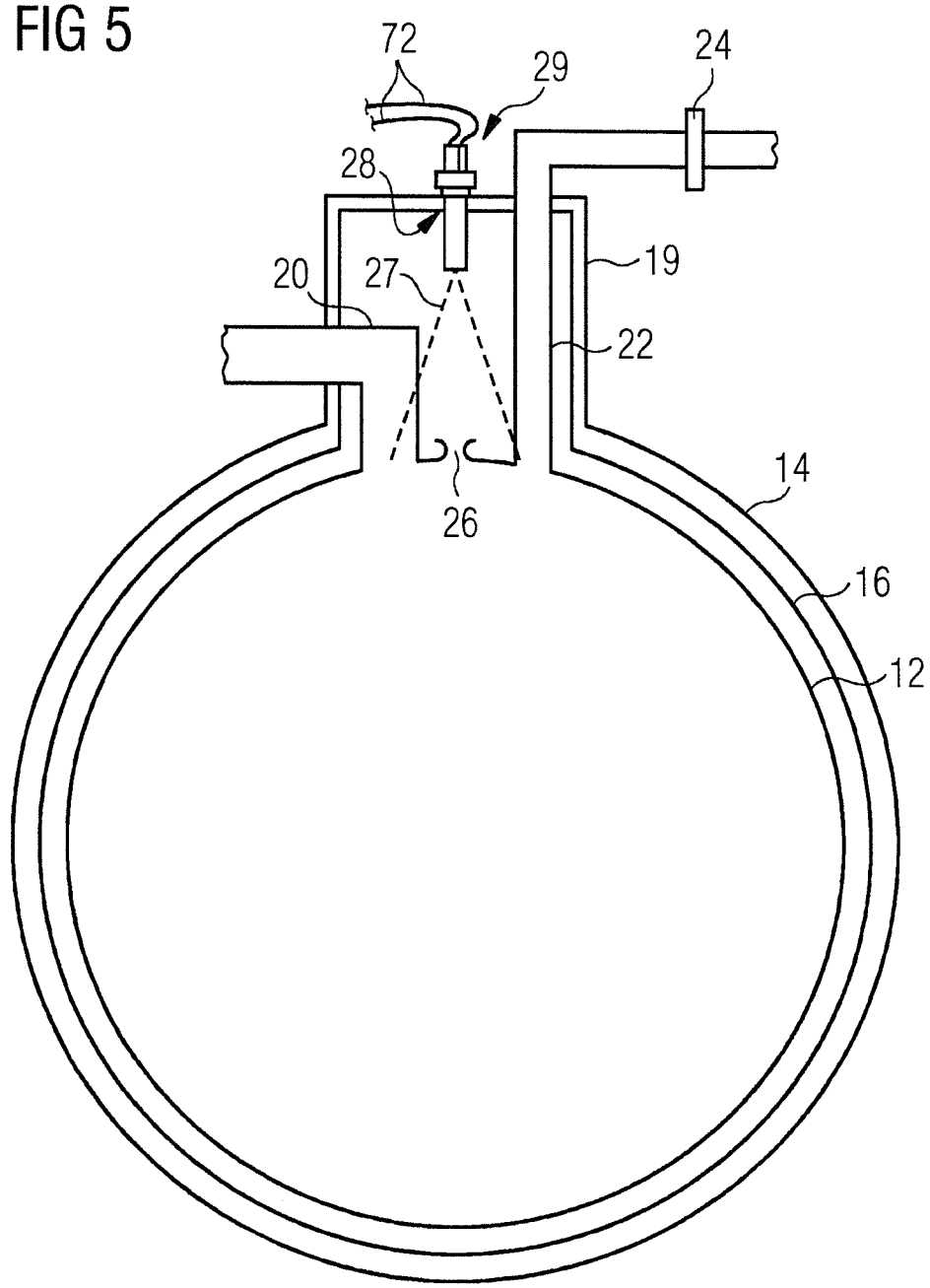
FIG. 5 shows a typical placement of a camera assembly of the present invention in a superconducting magnet such as shown in FIG. 1.

FIG. 5 schematically illustrates a cross-section of a cryostat, modified according to an embodiment of the invention. Features corresponding to features of FIG. 1 carry corresponding reference numerals.

In the illustrated cryostat, an auxiliary vent tube 22 is provided, passing from cryogen vessel 12 through turret 19. A burst disc or similar 24 seals the auxiliary vent, but will burst allowing egress of cryogen through the auxiliary vent in case of excess pressure within the cryogen vessel while the main vent tube 20 is blocked for any reason. A siphon cone 26 is shown. When the cryogen vessel 12 is to be filled with cryogen, a siphon funnel or siphon tube is introduced through a hole 28 in an upper wall of the turret, and is located into the siphon cone 26. Cryogen is then introduced into the cryogen vessel through the siphon funnel or tube and the siphon cone 26. Once cryogen filling is complete, the siphon tube or siphon funnel is removed, and the hole 28 is blocked with a bung (not shown).

According to an embodiment of the present invention, a camera 29 is positioned in place of the bung. Illumination is provided with the camera, and provides an image of field of view 27. In this arrangement, field of view 30 includes a view of siphon cone 26, which is generally regarded as a likely site for ice formation.

The present invention provides camera, typically a small digital camera such as a CCD camera as commonly used in mobile telephones, for location into the turret of the cryostat of an MRI magnet to enable observation of any ice which may build-up in the area around the siphon fill cone. Such camera may be left in place permanently, in which case it can be used to capture images at any time. Alternatively, the camera may be placed in position only when image capture is required. Captured picture data can be downloaded to a remote location for review either by a technician or operator, or for automatic analysis by a computer based image analysis method. Data relating to operational parameters such as magnet temperatures, cryogen level etc. may also be sent at the same time.

Image processing software, either at the MRI system or at a remote location, may review image data provided by the camera to provide an automated detection of changes in the picture, which may be arranged to signal to a user or a service technician that ice build-up may be occurring.

By providing early indication of a build-up of ice, for example on the siphon cone in the illustrated embodiment, health and safety risks to the user will be reduced. Quick diagnosis of ice build-up can enable a local service technician to attend and carry out a relatively minor rectification, rather than a complete on-site investigation which may be required if ice is permitted to build-up too far. Such investigation would prove to be costly in terms of service time and cost and MRI system down time.

Conventionally, MRI magnets have a standard siphon bung in the turret to close the cryogen vessel from atmosphere. According to the present invention, a digital camera can be fitted in place of the bung very quickly, with the magnet at field. For example, the camera may be placed in position at regular intervals as determined by a maintenance schedule. No specialist knowledge is needed to interpret images captured by the camera, as the image may be transferred to a remote service centre, for example at the manufacturer of the magnet, practically instantly over the internet or the telephone network. The service centre can study the captured images, either manually or automatically, and can signal any detected problems back to the user.

For example, each local service technician may be provided with a digital camera that fits the siphon port on the turret, a 5-6 meter USB lead and a computer for the camera to be connected to.

In an alternative arrangement, particularly suitable for retro-fitting to existing MRI magnets, a siphon bung may be adapted to accept a small digital camera. Preferably, the bung would be provided with a sealed window allowing the camera to capture images of the siphon fill cone, and further provided with sealed light ports or windows to provide illumination of the scene for the camera. The camera would plug into the adapted bung without the need to remove the bung at magnet pressure and magnetic field. The adapted bung may accordingly remain in place semi-permanently, the camera being added when required to capture images. The bung should be arranged to seal against the siphon cone to provide a gas seal and to seal against light intrusion from the exterior, and also light from the light source(s) reaching the camera lens directly.

Figure 2:
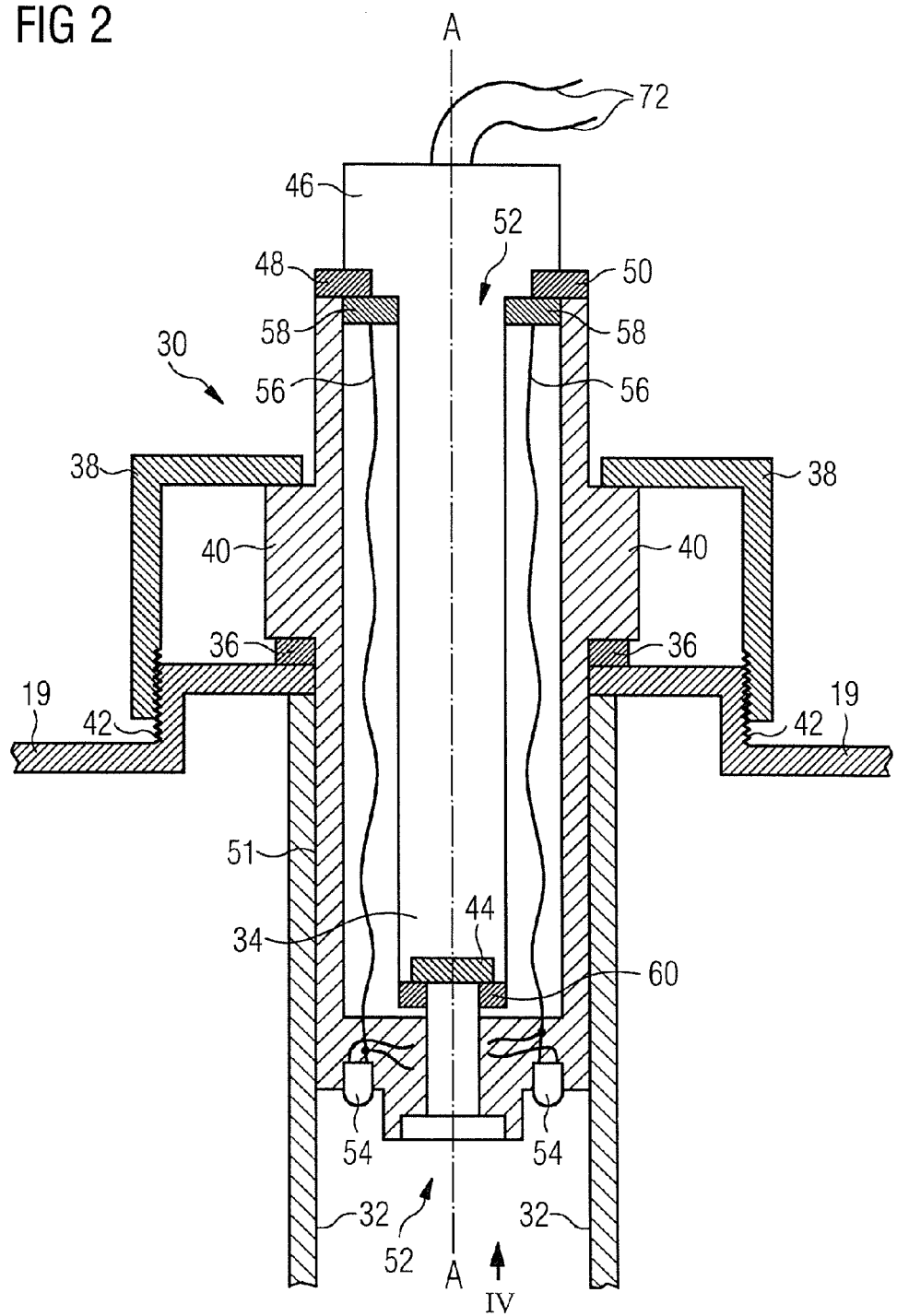
FIG. 2 illustrates a camera assembly according to an aspect of the present invention.

FIG. 2 illustrates a camera in camera housing 34 mounted into a bung body 30 according to an embodiment of the invention. The bung body is dimensioned to fit snugly into a siphon fill tube 32. The bung body should fit tightly enough that the alignment of the camera is predictable and repeatable. FIG. 2 illustrates a camera housing 34 which accommodates the camera sensor and associated lens(es) along with support circuitry such as a rechargeable battery and data communication interface.

Preferably, the bung body 30 seals the siphon tube 32 to the upper wall of the turret 19 in a gas-tight manner, for example using a copper washer 36. The bung body 30 may be held in place, and the copper washer 36 held under pressure, by retaining nut 38 acting on a retaining flange 40 of the camera housing 34, and tightened onto a threaded portion 42 encircling an opening of the siphon cone/tube 32.

Preferably, the camera housing 34 is detachable from the bung body 30, so that the bung body 30 may be left in place long term, and the camera housing 34 inserted into the bung body only when required for capturing an image.

FIGS. 3A and 3B show the bung body 30 and the camera housing 34 detached from one another. The camera housing 34 may be a standard commercially available camera housing, or may be specifically designed for use according to the present invention. The following description of camera housing and bung body arrangements is only an example, and many variants may be determined by those skilled in the art.

The camera housing 34 is essentially cylindrical, about an axis A-A (FIG. 2). At one end of the housing 34, a lens or window 44 is provided, to allow light to enter the camera housing to reach a camera sensor (not illustrated). The camera housing 34 will contain a camera sensor and associated optics conventionally arranged to capture image data representing light entering the lens or window 44. At the other end, an accessible part 46 is provided for handling of the camera housing. Separate or combined power and data lead(s) 72, for example a combined power and data lead according to the common USB standard, is/are provided. The lead(s) may be detachable. Alternatively, power for the camera may be provided from a power source internal to the camera housing, such as a rechargeable or disposable battery. Data communication to and from the camera may alternatively be by any appropriate wireless method, for example according to the Bluetooth® standard. Data may be provided to, and power provided from, a computer or a diagnostic system.

Preferably, electrical contacts 48, 50 are provided, accessible from the exterior of the camera housing 34. The purpose of these contacts will be described below. These contacts are connected to the camera's power source—such as the USB connection or internal batteries mentioned above.

Bung body 30 includes an axially elongate cavity 52 dimensioned to receive a part of the camera housing 34. Preferably, accessible part 46 of camera housing 34 remains outside of the cavity, allowing a user to easily manually insert and remove the camera housing into/from the cavity 52. The cavity may be lined with a compliant material 53 such as felt or neoprene foam to retain the camera housing 34 without risk of damage. The bung body 30 is shaped and dimensioned to have an insertion piece 51 of cross-section which is a snug fit into the siphon cone/tube 32, and to have a retaining flange 40 of greater cross-section than the insertion piece 50, to provide a positive location of the bung body into the siphon tube 32. As shown in FIG. 2, the retaining flange 40 may also bear upon a sealing washer 36 to provide a gas-tight seal between the bung body 30 and the upper wall of the turret 19. Alternatively, an o-ring or similar may be recessed into the insertion piece 32 to provide this function. The retaining flange 40 may provide a useful grip for manual insertion and removal of the bung body, and so may be knurled or have another surface treatment to provide an effective grip.

The bung body 30 has a sealed window 52 at a lower end, which in use is aligned with the window or lens 44 in the camera housing 34. The lower end also includes one or more light source 54 directed essentially parallel to the axis A-A to provide illumination of the scene for the camera. Conveniently, these light sources may be LEDs. They may be powered by the power source provided for the camera, in which case conductors 56 and contacts 58 are provided so that, in use, the light source(s) 54 are powered through contacts 48, 50 on the camera housing. In embodiments where the camera is removable, no controls are required for the light source. When the camera housing 30 is inserted into the cavity 52, contacts 48, 50 touch contacts 58 and the light source(s) 54 illuminate(s) while the camera is in position. The camera may be used to capture image data, and is then removed, removing the source of power to the light source(s). Preferably, the light source(s) can be controlled to emit more or less light. That can be achieved by controlling the power supplied to the light sources through contacts 48, 50. The power may be controlled remotely by a host system, or may be controlled locally by the camera to provide a required level of illumination for optimum image capture.

Preferably, as shown, a light seal 60 is provided, to prevent light from reaching the camera lens or window 44 other than through the window 52. Window 52 and light source(s) 54 must be sealed in a gas-tight manner to the bung body 30.

Figure 4:
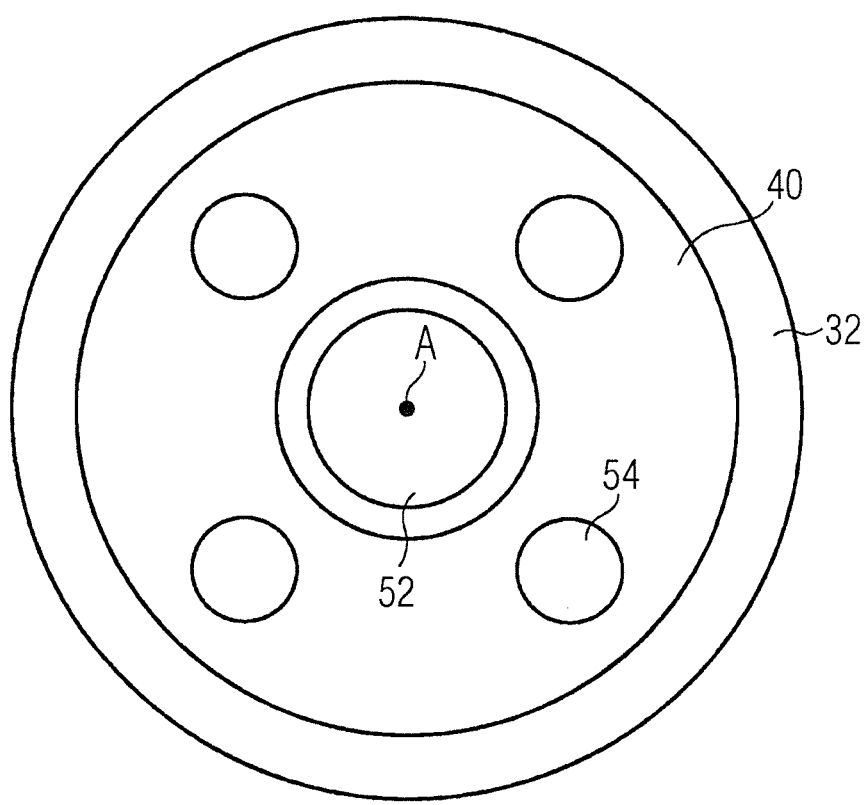
FIG. 4 shows an axial view of the component shown in FIG. 3B, in the direction IV.

FIG. 4 schematically illustrates an end-view of a lower end of the bung body 30 of FIGS. 2-3B, in the direction IV.

Digital software can give real time monitoring, and conventional picture recognition software could be used to provide a warning if changes occur. This would give an early warning to a problem so action can be taken. Typically, images captured by the camera would be stored in a diagnostic or monitoring system, and newly captured images compared to earlier images of the same scene so that changes may be detected. In other embodiments, the picture recognition software and image memory may be built in to the camera housing, so that a change in the scene may be detected and an alarm condition indicated by a portable camera housing without the need for a host system.

Use of the camera according to the present invention does not require the magnet to be de-energised, allowing checks for ice build-up to be made with the magnet at field. To allow use of the camera with the magnet at field, the camera and the camera housing should be free of magnetic materials as far as possible.

Since the use of the camera of the present invention is relatively straightforward, a camera may be provided to local service technicians, who can easily capture an image of the siphon tube or other region of interest and provide it to a supervisory system, for example held by the manufacturer. The supervisory system may be programmed to perform an image recognition step to detect any changes. If a change is detected, particularly one which suggests ice build-up, then this can be communicated back to the service technician for rectification. If communications networks such as the internet and/or mobile telephone networks are available, this may be carried out in near-real time, avoiding the need for a further service visit and a second period of system downtime.

Checks for ice formation using the apparatus of the present invention may be performed during regular service visits, or even just between MRI scanning operations. No additional down-time will be required for the ice checking according to the present invention.

Ice monitoring according to the present invention may be carried out more regularly than in the usual service schedule, and ice build-up may be detected sooner than in conventional service schedules. Early detection means that the build-up of ice may be removed relatively easily as compared to the lengthy warm-up procedures conventionally used.

Accordingly, the number of magnets which would require warm ups and extensive repairs to remove ice build-up is reduced. This is a significant cost saving, and gives the user an improved service and reliability of their MRI system.

Conventionally, to remove an ice build-up, it was necessary to allow the siphon cone 26 to warm up, during which time a significant amount of cryogen such as helium may be lost. According to the present invention, smaller build-ups of ice may be detected and may be removed without requiring a complete warm-up of the siphon cone. The bung body 30 remains in place and so little if any cryogen is wasted as a result of insertion, removal and use of the camera of the present invention. It may be expected that use of the present invention will reduce whole-life cryogen consumption for an MRI system.

The camera housing is designed to protect the camera sensor so that it can work in a cryogenically-cooled environment without harm. The bung body 30 may be designed to fit into siphon tubes or other chosen locations within existing MRI systems without redesign or adaptation of any existing components.

The present invention provides embodiments within at least the following variants:

1) a camera built into a siphon bung, the camera being put in position when an image is required, then removed and replaced with a standard bung at other times; and 2) a specially adapted bung with cavity for accepting a portable camera, but the camera is only placed in position when an image is to be captured. At other times, only the specially adapted bung is in the siphon tube/cone. Alternatively, a standard bung may be put in place when image capture is not required.

Positioning in a bung 30 located in the siphon tube 32 is simple and, with typical designs, gives adequate view 29 of the likely icing position at the siphon cone 26.

In all cases, the siphon tube is bunged, either by a special bung housing, either for housing a camera 34 or with a built-in camera; or by a normal bung in cases where the camera is located elsewhere.

In newly designed magnets, the camera may be positioned at a selected location to give an optimal view 29 of the likely position of the icing of the siphon cone 26.

As the camera 34 can be produced relatively inexpensively, it is possible to provide a dedicated camera for each cryostat, and to perform remote detection of icing without the need to despatch specialist equipment to site. The camera may be available with on-site maintenance equipment. A local service technician can capture useful images and send them to a remote engineer for analysis and planning of further action where necessary. The capturing of images is so rapid that it can be performed between scan sequences, with no need for down-time unless a problem is detected.

In embodiments where the camera and bung body are a single object: the camera is in a body which fits snugly into the siphon tube. When an inspection is required, the standard siphon tube bung is removed, and the camera body inserted in its place as quickly as possible. In another alternative, the bung body of FIGS. 2-3 is removed and inserted with the camera, and a standard bung is put in place whenever an image capture is not required.

Figure 6:
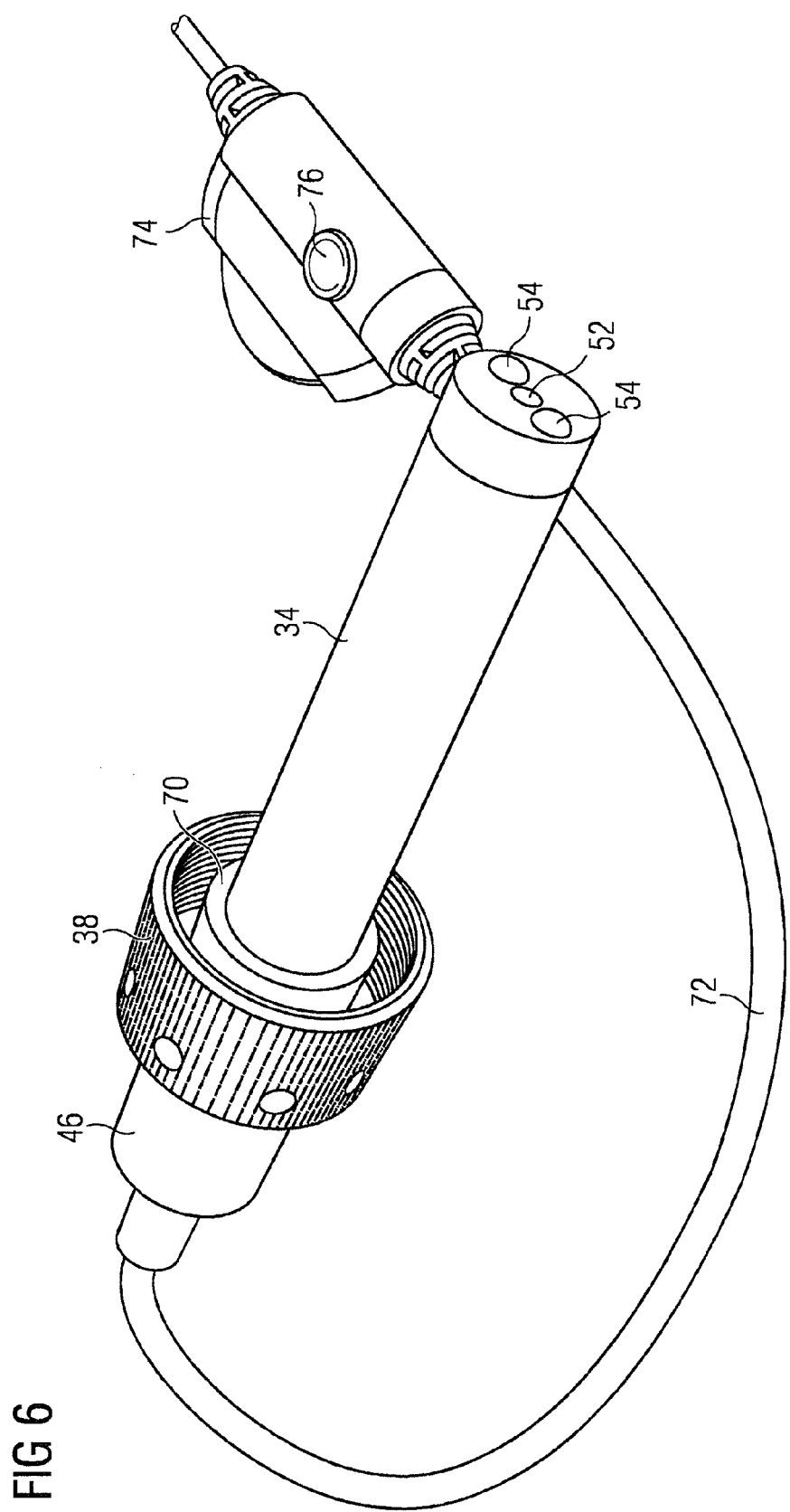
FIG. 6 shows a combined camera and light source.

FIG. 6 shows a picture of a combined camera and light sources 54 and camera window 52 are clearly visible. An o-ring 70 is provided for gas-tight sealing when the camera is in position. The power/data lead 72 includes a control switch arrangement 74, which may include one or more switches 76 for: turning the illumination on or off; varying the intensity of the illumination; capturing and storing or transmitting image data. The accessible part 46 in this embodiment has a rubber covering to assist with manual handling. The body of the camera 34 acts as a mechanical and gas-tight shield, so that the camera sensor will not be damaged by exposure to cryogen gas, or mechanically damaged due to rough handling.

Known alternative arrangements for capturing images of siphon cones for the purpose of detecting ice deposits require expensive and delicate equipment, which is unsuitable for use by local field service technicians, and typically require the magnet to be run down to zero field, in turn requiring a bulky and expensive magnet power supply on site, and involving a significant consumption of cryogen. The camera assembly of the present invention may be constructed essentially of non-magnetic materials, allowing the camera to be used with the magnet at field.

Figure 7:
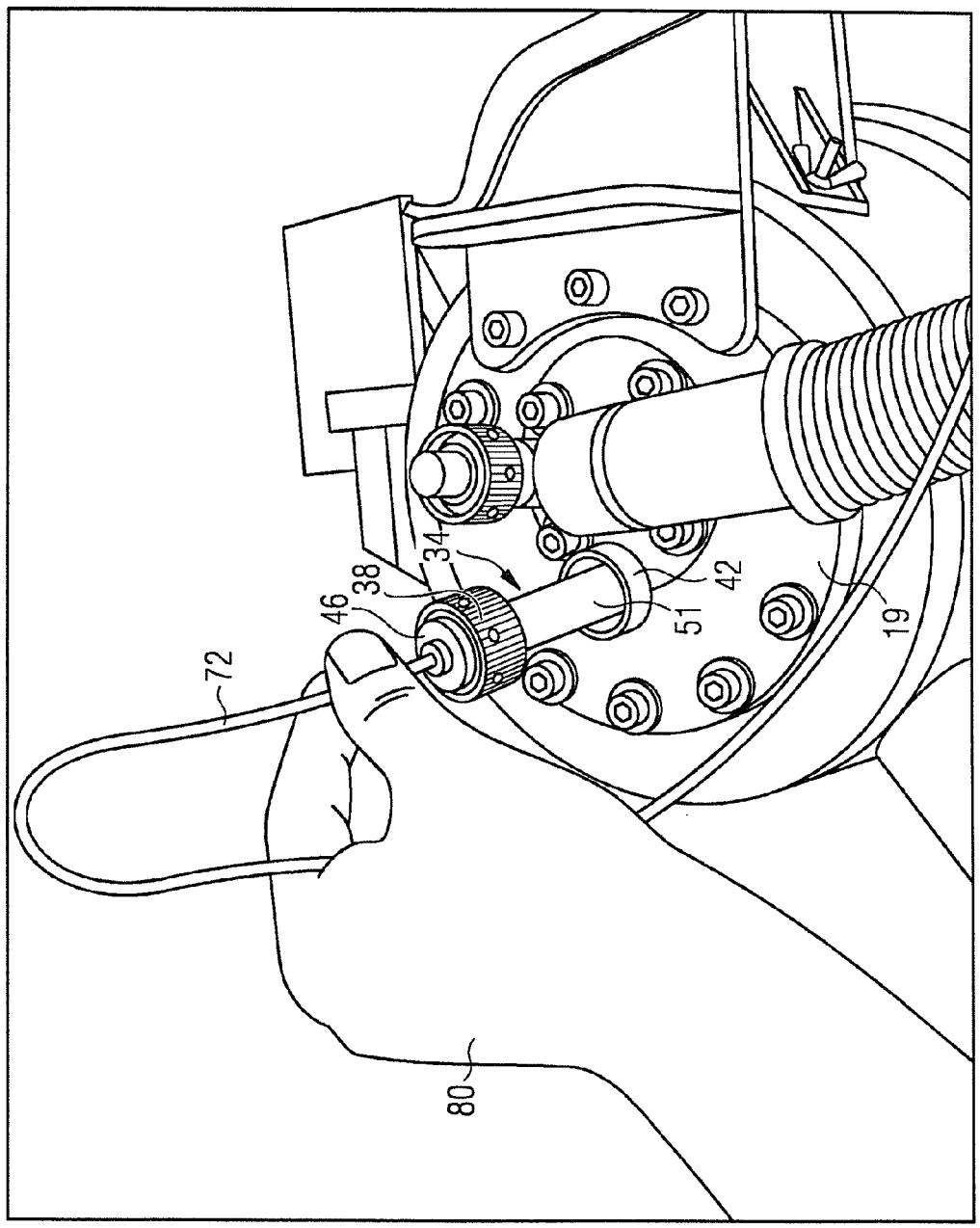
FIG. 7 shows a service technician inserting a camera of the present invention into a superconducting magnet.

FIG. 7 shows a technician 80 inserting lower part 51 of camera housing 34 into a siphon tube of a cryostat.

Figure 8:
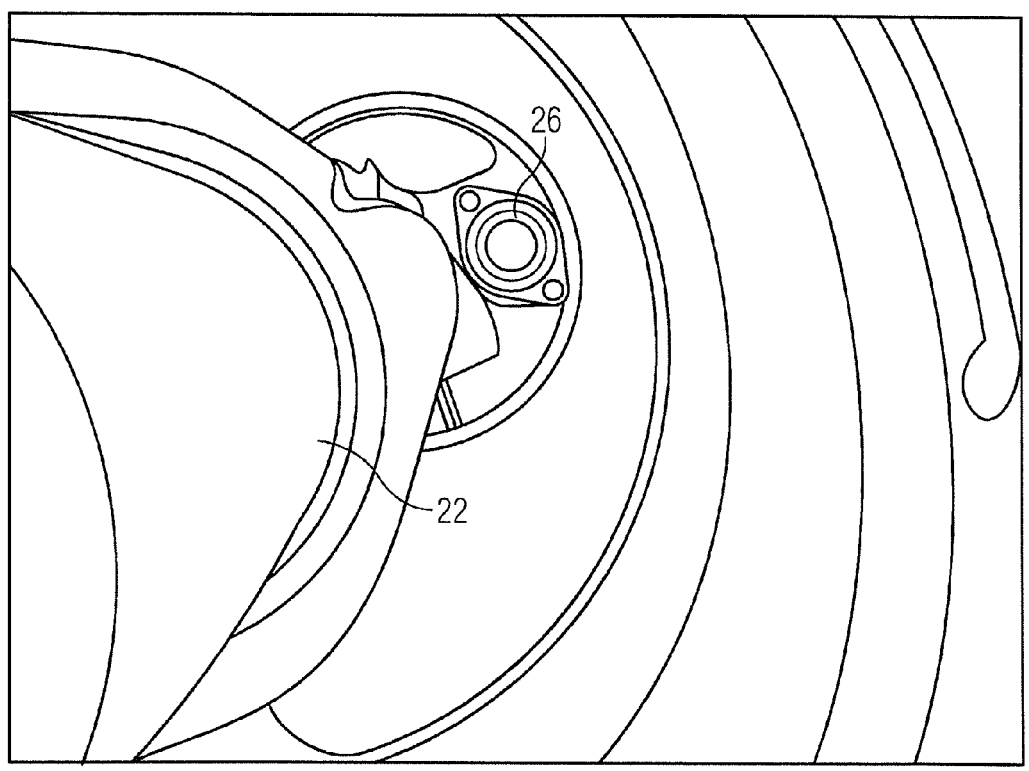
FIG. 8 shows a typical view observed by a camera used according to the present invention.
Figure 9:
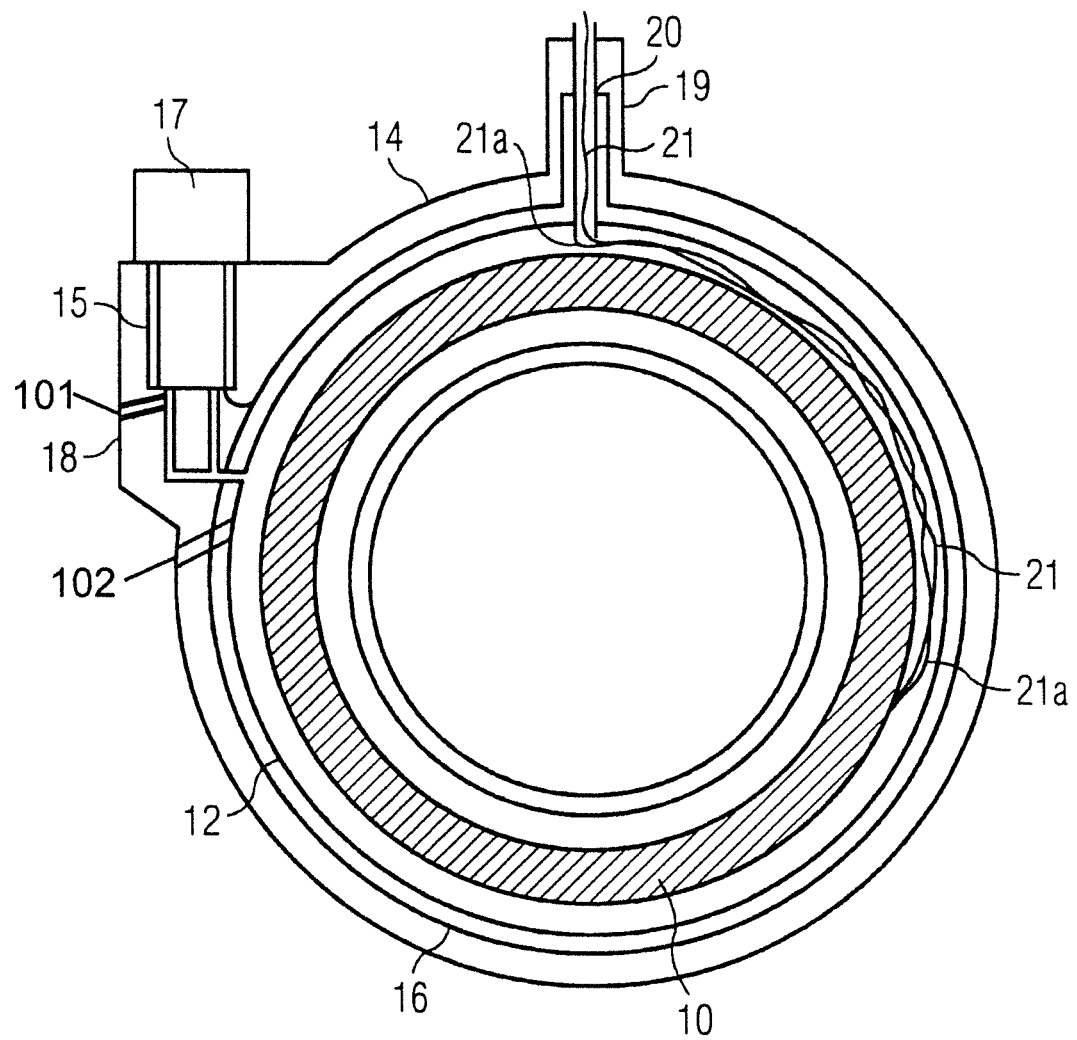
FIG. 9 is a duplicate of FIG. 1, wherein possible locations are designated for bung assemblies according to the present invention.

FIG. 8 shows an example image which may be captured by the camera of FIG. 7, showing a clear siphon cone 26, free of ice.

In certain embodiments of the invention, a suitable port may be provided to allow the camera 34 to observe other regions where ice deposits are likely to occur. For example, any regions cold enough to cause water vapour to freeze. FIG. 10 shows a copy of FIG. 1 marked with example locations for bung assemblies according to the present invention. At position 101, a port may be provided in the cryostat to locate a bung assembly of the present invention to observe a first cooling stage of refrigerator 17, and the thermal interface with thermal radiation shield 16. At position 102, a port may be provided in the cryostat to locate a bung assembly of the present invention to observe a surface of magnet 10 in the vicinity of a connection between cryogen vessel 12 and refrigerator sock 15. Such ports at positions 101, 102 may also be used for de-icing operations if the bung assembly of the present invention is removed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for performing remote detection of ice formation within a cryostat, comprising:
   providing a bung assembly for closing a hole in a turret of a cryostat, said bung assembly comprising a camera housing and a bung body mechanically dimensioned to fit the hole and provided with a sealing arrangement for forming a gas-tight seal between the bung body and the turret;
   capturing a current image generated by the camera sensor;
   in a processor comparing the current image to a similar reference image of the same field of view taken at an earlier time; and
   in said processor evaluating differences between the current and reference images to detect growth of ice formation.

2. A method according to claim 1 wherein said comparing comprises:
   transmitting the current image to a remote location, where a user can retrieve the current image and the reference image for comparison.

3. A method according to claim 1 comprising using a computer implemented method to detect differences between the current image and the reference image.

4. A bung assembly for closing a hole in a turret of a cryostat, said bung assembly comprising a camera housing and a bung body mechanically dimensioned to fit the hole and provided with a sealing arrangement for forming a gas-tight seal between the bung body and the turret.

5. An assembly according to claim 4 wherein the camera housing is removable from the bung body, such that the bung body alone seals the hole siphon port.

6. A method according to claim 4 wherein the bug body further comprises a light source, and the light source is powered by a power supply which also powers the camera sensor.

7. A bung assembly according to claim 4 wherein, in use, the camera has a field of view that includes a view of an opening of a cryogen vessel within the cryostat.

8. A bung assembly according to claim 7 wherein the opening is defined by a siphon cone, and the hole closed by the bung is an opening of a siphon tube aligned with the siphon cone.

* * * * *